United States Patent
Fagin et al.

(10) Patent No.: US 10,045,704 B2
(45) Date of Patent: Aug. 14, 2018

(54) METHOD FOR LAPAROSCOPIC NERVE DETECTION AND MAPPING

(75) Inventors: Randy Fagin, Austin, TX (US); Jon Schiff, Austin, TX (US); Jann Bonfils-Rasmussen, Leander, TX (US)

(73) Assignee: ProPep, LLC, Austin, TX (US)

( * ) Notice: Subject to any disclaimer, the term of this patent is extended or adjusted under 35 U.S.C. 154(b) by 873 days.

(21) Appl. No.: 13/290,035

(22) Filed: Nov. 4, 2011

(65) Prior Publication Data
US 2012/0059275 A1   Mar. 8, 2012

Related U.S. Application Data

(62) Division of application No. 11/745,505, filed on May 8, 2007, now Pat. No. 8,083,685.

(51) Int. Cl.
| | |
|---|---|
| *A61B 10/00* | (2006.01) |
| *A61B 5/103* | (2006.01) |
| *A61B 5/117* | (2016.01) |
| *A61B 5/04* | (2006.01) |
| *A61B 5/00* | (2006.01) |
| *A61B 34/30* | (2016.01) |

(52) U.S. Cl.
CPC ........ *A61B 5/04001* (2013.01); *A61B 5/4041* (2013.01); *A61B 34/30* (2016.02); *A61B 2034/301* (2016.02)

(58) Field of Classification Search
CPC .................................................. A61B 5/4893
USPC ........ 600/554, 546, 547, 427, 372, 301, 562, 600/564, 566, 567, 587
See application file for complete search history.

(56) References Cited

U.S. PATENT DOCUMENTS

| | | | |
|---|---|---|---|
| 6,139,545 A | 10/2000 | Utley et al. | |
| 6,810,281 B2 * | 10/2004 | Brock et al. | 600/427 |
| 2003/0158545 A1 * | 8/2003 | Hovda et al. | 606/32 |
| 2007/0060921 A1 * | 3/2007 | Janssen et al. | 606/41 |
| 2011/0270120 A1 | 11/2011 | McFarlin et al. | |

OTHER PUBLICATIONS

Lodish et al., "Section 21.2 The Action Potential and Conduction of Electric Impulses," Molecular Cell Biology, 2000, 4th edition, W.H. Freeman, New York, https://www.ncbi.nlm.nih.gov/books/NBK21668/.

* cited by examiner

Primary Examiner — May Abouelela
(74) Attorney, Agent, or Firm — Trop, Pruner & Hu, P.C.

(57) ABSTRACT

A surgical method aids identification of nerves in a body to help prevent damage to the nerves during surgery to the body proximate the nerves. An electrode introduced to within a body cavity through a catheter is placed proximate a nerve within the body cavity by a laparoscopic or robotic device. An exploratory probe placed in the body cavity is selectively placed along a presumed pathway of the nerve to provide an electrical signal through the nerve to the electrode. An analyzer interfaced with the electrode analyzes the electrical signal received at the electrode to determine the proximity of the exploratory probe to the nerve, allowing mapping of the nerve pathway through the body cavity.

4 Claims, 5 Drawing Sheets

METHOD FOR LAPAROSCOPIC NERVE DETECTION AND MAPPING

CROSS REFERENCE TO RELATED APPLICATION

This application is a divisional of U.S. patent application Ser. No. 11/745,505, filed May 8, 2007 and entitled "System and Method for Laparoscopic Nerve Detection", which issued as U.S. Pat. No. 8,083,685 on Dec. 27, 2011. The content of the above application is hereby incorporated by reference.

BACKGROUND OF THE INVENTION

Field of the Invention

The present invention relates in general to the field of laparoscopic surgery, and more particularly to a method for detection and mapping of internal nerve tissue.

Description of the Related Art

Traditionally, surgery on internal body parts is performed by cutting an incision in the skin to access the internal body parts. Such open surgery entails a number of known risks including infection, inadvertent damage to other organs and structures, scarring, and loss of blood. In an effort to reduce some of these risks and improve patient outcomes surgeons have developed laparoscopic, and more recently robotic, techniques to perform surgery. Robotic surgery is essentially an advanced type of laparoscopic surgery in which the arms that enter the body cavity are robotically controlled instead of manually controlled. During a laparoscopic or robotic surgery, small incisions are made in the skin through which 5-12 millimeter access ports are placed. These ports serve as doorways through which small working instruments and a camera can be placed. The camera creates a magnified view of the internal organs that the surgeon sees on a monitor or console. Such less invasive laparoscopic and robotic surgeries typically have reduced side effects for the patient to allow a more rapid and complete recovery.

One example where laparoscopic and robotic surgery has gained acceptance with positive results is for the accomplishment of a radical prostatectomy. Conventionally, a radical prostatectomy is performed by cutting an incision at the base of the pelvic bone to gain access to the prostate. Once visible, the prostate is cut from the surrounding tissue and removed. Because the area around the prostate is rich in nerves and muscles that support sexual and urinary functions, a radical prostatectomy can cause severe side effects, including sexual dysfunction and incontinence. For example, up to half of conventionally-performed radical prostatectomies result in permanent erectile dysfunction. In contrast, a radical laparoscopic or robotic prostatectomy has the potential for far fewer side effects. In part, laparoscopic and robotic prostatectomies tend to have fewer side effects because the procedure affords the surgeon improved vision and in the case of robotics in particular, more dexterous tools as well. In the case of robotic surgery the improved vision and dexterity of the tools permits a skilled surgeon to better preserve sexual function nerves with as few as ten percent of patients being impotent as a result.

Although laparoscopic and robotic surgery has shown promising potential in reducing erectile dysfunction as a side effect of prostate gland removal, erectile dysfunction does still occur. In some instances, erectile dysfunction after a laparoscopic or robotic prostatectomy cannot be prevented due to Wallerian degeneration of nerves after even a slight injury. However, in some cases erectile dysfunction results from inadvertent damage done to the neurovascular bundle (NVB) that supports erectile function because the NVB is not where the surgeon expects. Direct visualization and appearance of the presumed NVB has not traditionally been a good indicator of preserved erectile nerves. The NVB travels from the base of the prostate where it joins with the bladder, to the apex (the portion where the urethra enters the penis). These nerves travel on opposing sides in a symmetrical fashion on the outside of the prostate capsule on its undersurface at the four and eight o'clock positions. Previous attempts at nerve monitoring during radical prostatectomy used electrical stimulation along the NVB with measurement of the signal in the cavernous bodies via a measurement of intracavernous pressures, i.e., muscle response to electrical stimulation. This method is not time efficient and recent studies have indicated that outcomes are inconsistent with the intraoperative findings.

SUMMARY OF THE INVENTION

Therefore a need has arisen for a rapid and precise system and method which aids in the detection and mapping of nerves during laparoscopic surgery.

In accordance with the present invention, a system and method are provided which substantially reduce the disadvantages and problems associated with previous methods and systems for performing laparoscopic surgery with reduced risk of damage to internal nerves, such as laparoscopic prostate removal with reduced risk of damage to erectile nerves. A probe inserted through the body surface with a catheter and into a body cavity is accessible by a laparoscopic device for placement proximate a nerve. A second probe placed along a presumed pathway of the nerve completes an electrical circuit with the first probe through the nerve so that an electrical signal communicates between the probes. Analysis of the electrical signal supports mapping of the approximate nerve pathway through the body cavity.

More specifically, in a first embodiment of the electrode probe delivery device of this invention, as depicted in FIGS. 1-3, a handle has one or more catheters providing conduit(s) for inserting electrode probes (electrodes) through a body surface (e.g. abdominal wall) and into a body cavity. The electrode probes pass through the catheters and into the body cavity to be accessible for manipulation by a laparoscopic or robotic device. Under the control of a surgeon, a separate and distinct laparoscopic or robotic device is used to pull the electrode probe(s) into the body cavity for coupling to the body tissue proximate a selected nerve of interest. An exploratory probe inserted into the body cavity (e.g. the abdomen) through a laparoscopic channel introduces an electric signal into the tissue of a surgery subject proximate the presumed nerve pathway. This signal is received by the electrode probe coupled to the tissue proximate the nerve of interest. Because nerve tissue conducts electrical current better than do other body tissues, the relative strength of the electrical signal passing through the nerve and recorded at the electrode probe will increase as the exploratory probe is placed closer to the nerve to which the electrode probe is coupled. An analyzer interfaced with the electrode probe provides an indication of the proximity of the exploratory probe to the nerve, such as an audible sound or visually-depicted signal that varies in intensity with the intensity of the electrical potential received at the electrode probe. Placement of the exploratory probe at various points along the presumed nerve pathway allows a mapping of the approximate actual nerve pathway by noting the points at which the electrical signal is relatively strongest. Being able to avoid the approximated nerve pathway while dissecting within the body cavity helps the surgeon reduce the risk of nerve damage.

In another embodiment of the method, an electrode probe inserted through the body surface via an introducer catheter, cannula or needle and into a body cavity (such as the abdominal cavity, for example) is accessible by a separate and distinct laparoscopic or robotic device for placement into muscle tissue where the nerve of interest terminates. An exploratory probe placed along a presumed pathway of the nerve introduces an electric current into the muscle tissue surrounding the nerve of interest causing a depolarization of the nerve which results in an action potential. The action potential then propagates along the nerve to the neuromuscular junction (the synapse between the nerve and the muscle cell) where a neurotransmitter (acetylcholine) is released in response to the action potential. This neurotransmitter depolarizes the postsynaptic muscle cells creating an electrical potential received by the electrode probe. Analysis of the electrical signal (electrical potential) supports mapping of the approximate nerve pathway through the body cavity.

The present invention provides a number of important technical advantages. One example of an important technical advantage is that nerve pathways internal to the body are detectable during laparoscopic and robotic surgery to help the surgeon avoid inadvertent damage to the nerves. Detection of nerve pathways is rapid and precise by variable signals, such as an audible tone or visual signal that reflect the proximity of a probe to the nerve pathway. Monitoring of nerve pathways is made possible throughout a surgical procedure with readily accessible probes managed with laparoscopic or robotic tools. Probe pairs provide convenient monitoring where nerves serve an area of interest, such as the pair of NVBs that travel from the four and eight o'clock positions under the prostate gland.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention may be better understood, and its numerous objects, features and advantages made apparent to those skilled in the art by referencing the accompanying drawings. The use of the same reference number throughout the several figures designates a like or similar element.

DETAILED DESCRIPTION

Selectively applying electrical current through a nerve within a body cavity allows a surgeon to map the position of the nerve's pathway through the body cavity. By having an approximate map of the nerve pathway, the surgeon is able to dissect regions of the body near the nerve with a reduced risk of damage to the nerve. Thus, for instance, cancerous portions of the body are surgically removed by selecting dissection points as distal to the nerve as is practical. One example of a dissection presented below is the dissection of a prostate gland from within the abdominal cavity using laparoscopic or robotic techniques. Identification of the neurovascular bundle (NVB) that supports erectile function helps to preserve those nerves that support erectile function after removal of the prostate gland. Repeated probing along the presumed pathway of the NVB proximate to the prostate gland maps the approximate location of the NVB, allowing the surgeon to select dissection points that reduce the risk of damage to the NVB. Although a prostate dissection is presented as an exemplary use of the mapping of a nerve pathway through a body cavity, other types of surgeries may benefit from application of the disclosed laparoscopic nerve mapping procedure. In addition, the use of electrode probes supports mapping of nerve pathways that are sometimes found both inside and outside of the body's skin surface.

Figure 1:
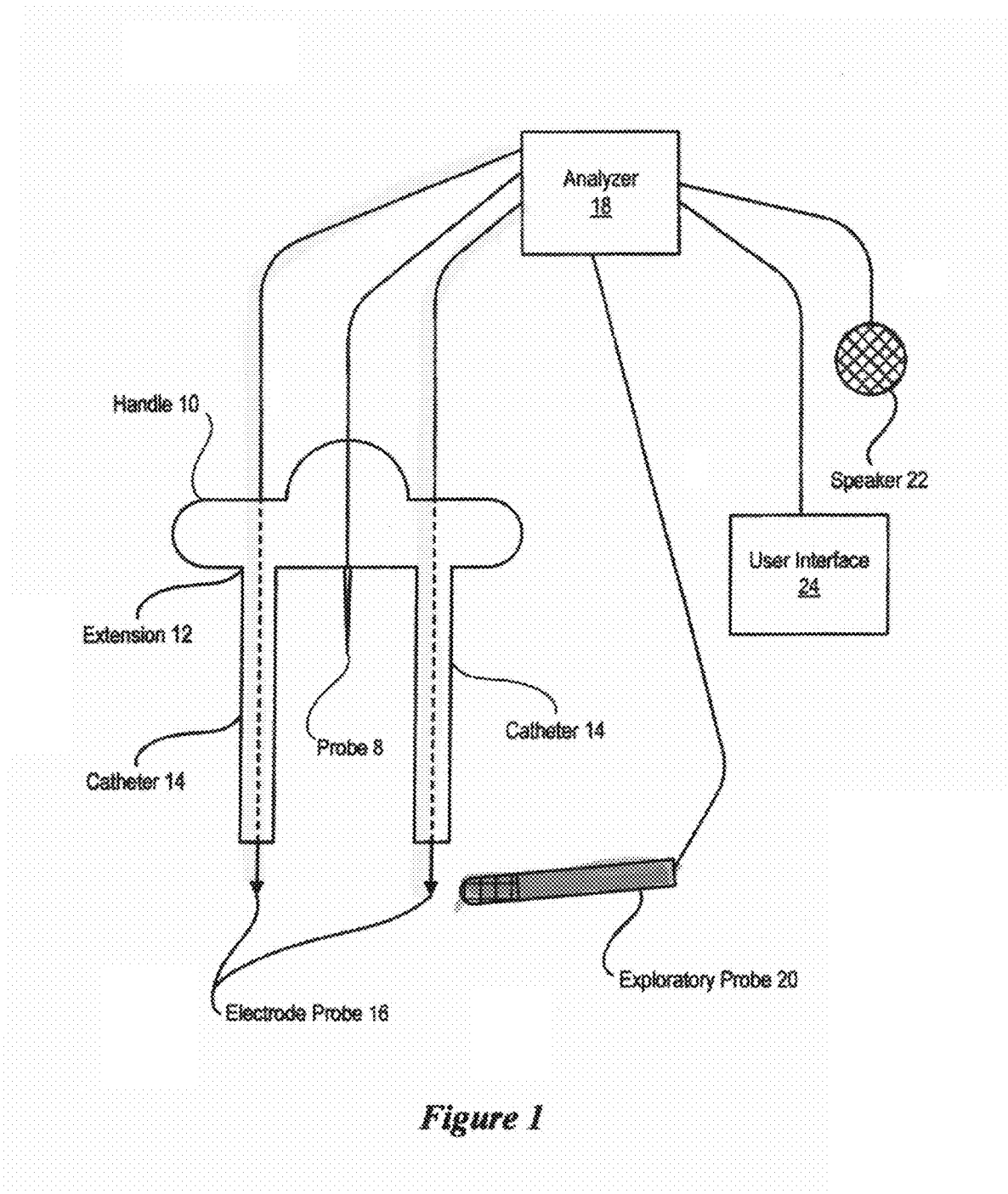
FIG. 1 depicts one embodiment of a system for identifying nerve pathways within a body cavity.

Referring now to FIG. 1, one embodiment of a system, generally designated 15, for identifying nerve pathways within a body cavity is depicted. An electrode probe delivery device 11 has a handle 10, a probe 8 and two extensions 12, each extension having an integrated catheter 14. Handle 10 and catheters 14 provide pathways through which electrode probes (flexible probe wires) 16 can be placed into the body cavity using a separate and distinct laparoscopic or robotic device. The electrode probed (16) can be coupled to tissue proximate a nerve of interest. Electrode probes 16 are shown in FIG. 1 extending past the end of catheters 14 where they are accessible for grasping by the laparoscopic or robotic device for placement as required. Electrode probes 16 are interfaced through another wire or other communication device (e.g. by radiofrequency transmission) with an analyzer 18 so that electrical signals, such as voltage and current levels, detected at each electrode probe 16 are communicated to analyzer 18. An additional ground probe 8 provides patient grounding when catheters 14 are inserted into the body by interfacing with analyzer 18 through a ground wire 13. Analyzer 18 interfaces with an exploratory probe 20 and selectively sends a predetermined electrical signal (such as a predetermined current) to exploratory probe 20. The electrical signal passes through exploratory probe 20 to the tissue of a surgery subject proximate a presumed nerve pathway and received by an electrode probe 16 coupled to the body at a point also proximate the presumed nerve pathway. Because nerve tissue conducts an electrical current better than other body tissues, the relative strength of the electrical signal passing through the nerve and recorded at an electrode probe 16 will increase as exploratory probe 20 is placed closer to the nerve to which the electrode probe 16 is proximately coupled. Thus, by moving exploratory probe 20 along the presumed nerve pathway, analyzer 18 approximately maps the actual nerve pathway based upon the strength of the signal recorded at electrode probe 16 for each position of exploratory probe 20.

The surgical system depicted by FIG. 1 is built from material adapted for use by laparoscopic and robotic devices to support mapping of nerve pathways through a body cavity. For example, handle 10 and catheters 14 are formed as an integrated unit (electrode probe delivery device 11) for one time use and disposal. For instance, handle 10 is formed from non-conductive hard plastic and catheter 14 is a large bore stainless steel needles, although other types of catheters or cannulae may suffice as introducers for the electrode probes, such as those made of rigid plastic, such as polycarbonate, for example, or flexible plastic such as polyurethane, for example. Electrode probes 16 are preferably thin, insulated wires which have a length sufficient to reach the desired area within the body cavity when grabbed by a separate and distinct laparoscopic or robotic device and pulled through catheter 14 to the desired area. As an example of dimensions that suffice for a prostatectomy, the length of catheters 14 extending from handle 10 is approximately between 45 mm and 65 mm. Electrode probes 16 are, for example, flexible recording electrodes suitable for manipulation by a laparoscopic or robotic device under direct laparoscopic vision, such as with an extendable length of approximately 50 cm from the end of catheter 14. Analyzer 18 interfaces with a speaker 22, which outputs an auditory signal having an interval and intensity related to the strength of the electrical potential detected at electrode probe 16. Thus, for example, a surgeon maps a nerve pathway by listening to the intensity of the auditory response output at speaker 22 and comparing the auditory responses of different positions of exploratory probe 20. Additionally, a user interface 24 can provide visual analysis of the nerve pathway as well as control over the signal provided at exploratory probe 20.

Figure 2:
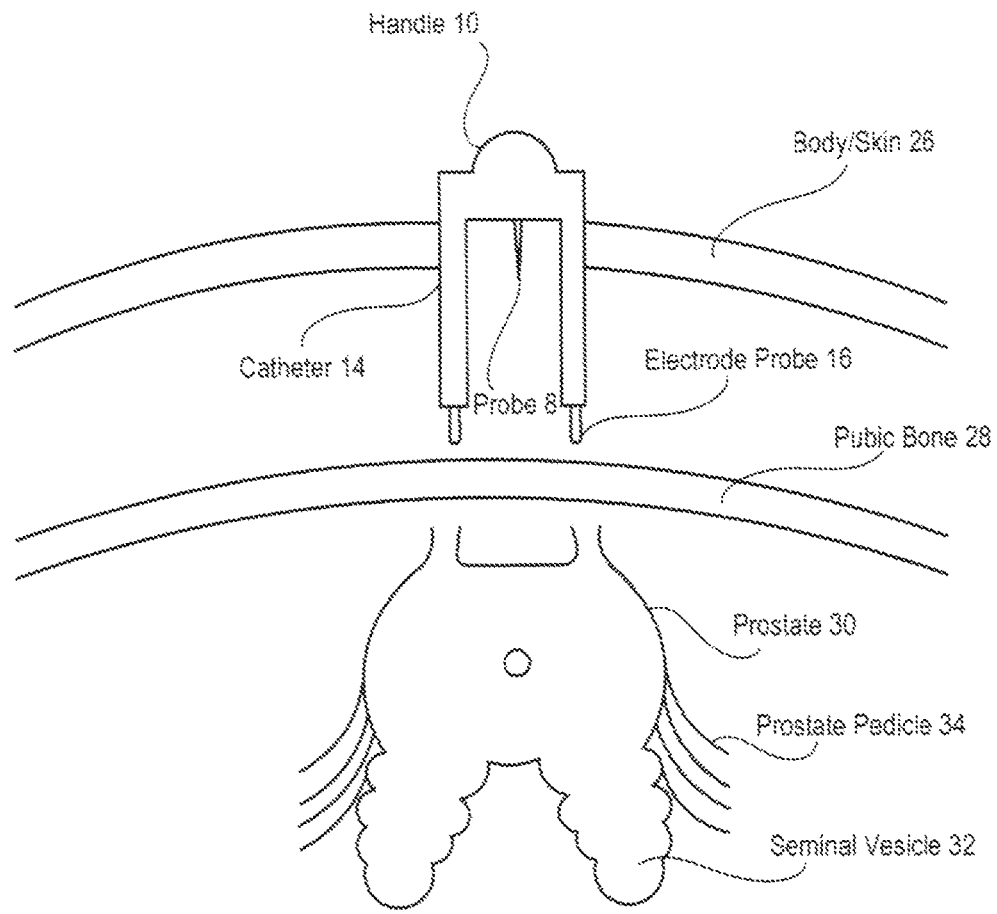
FIG. 2 depicts insertion of a dual electrode probe with a dual catheter through a body surface and into a body cavity.

Referring now to FIG. 2, insertion of an electrode probe delivery device 11 with a catheter 14 through a body surface and into a body cavity is depicted. Handle 10 is used to facilitate placement of the catheter(s) 14 through the abdominal wall into the abdominal cavity suprapubicly. Catheter 14 provides a conduit through abdominal wall 26 for introducing electrode probes 16 into the abdominal cavity. The pubic bone 28 sits above the prostate 30 and seminal vesicles 32 within the abdominal cavity. Dissection of prostate 30 requires cutting at the prostate pedicle 34, through which neurovascular bundles (NVBs) travel that support erectile function. During laparoscopic or robotic surgery, laparoscopic devices or robotic devices are inserted into the abdominal cavity to allow dissection of prostate 30.

Figure 3:
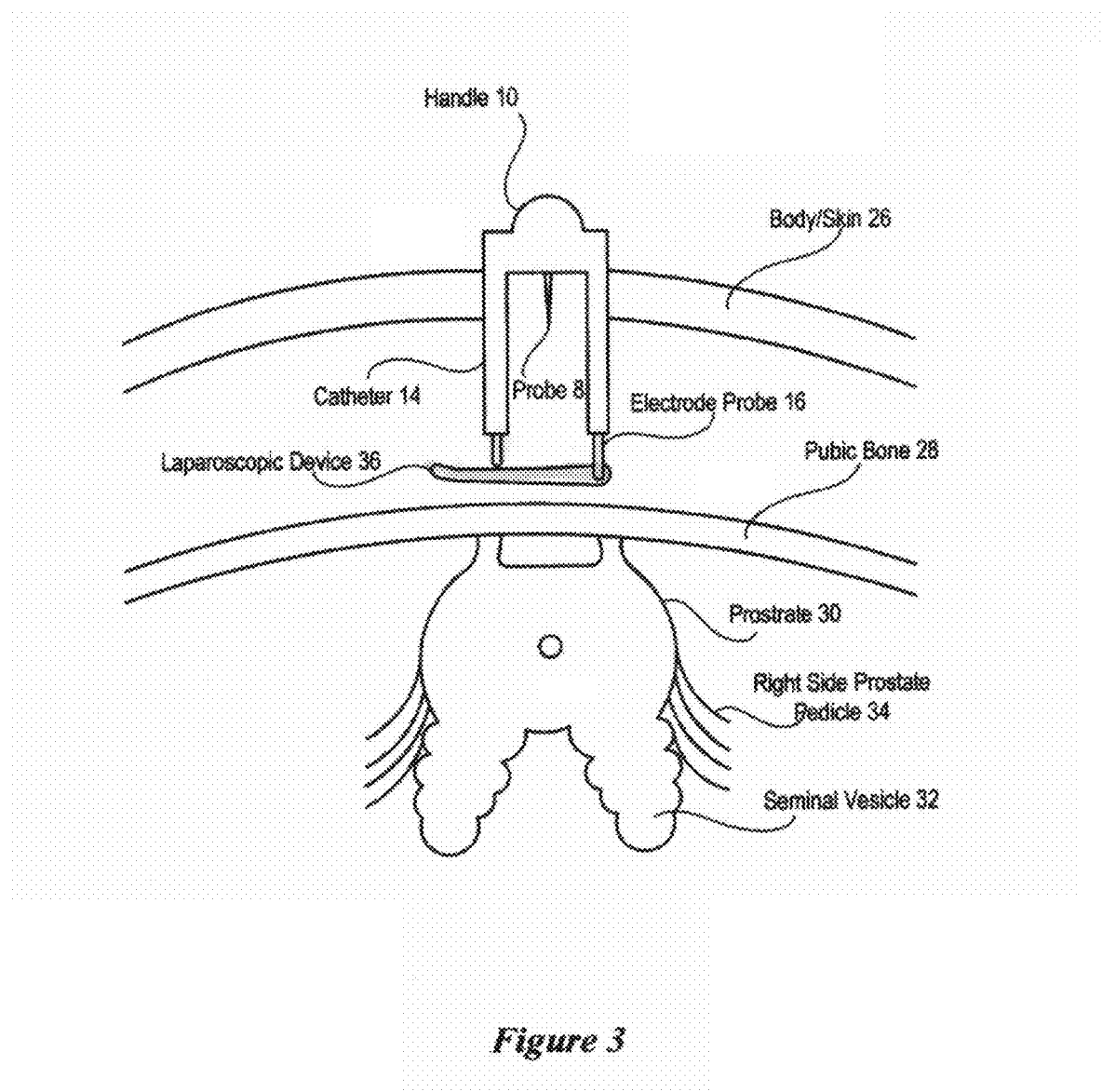
FIG. 3 depicts positioning of an electrode probe with a laparoscopic device to couple to the body within the body cavity proximate a nerve.

Referring now to FIG. 3, positioning of an electrode probe with a laparoscopic device to couple to the body within the body cavity proximate a nerve is depicted. Each catheter 14 allows safe insertion of self-contained recording electrode probe 16 where the probes 16 are visible to laparoscopic vision while simultaneously grounding the body through probe 8. Under direct laparoscopic vision, a laparoscopic device or robotic device 36 grabs electrode probe 16 to move probe 16 to a desired location proximate a nerve of interest. Laparoscopic device 36 advances the probe 16 on the right hand side to a position proximate the NVB on the right hand side of prostate 30 and advances the probe 16 on the left hand side to a position proximate the NVB on the left hand side of prostate 30. Probes 16 temporarily couple to the body so that they remain in position until removed by laparoscopic device 36.

Figure 4:
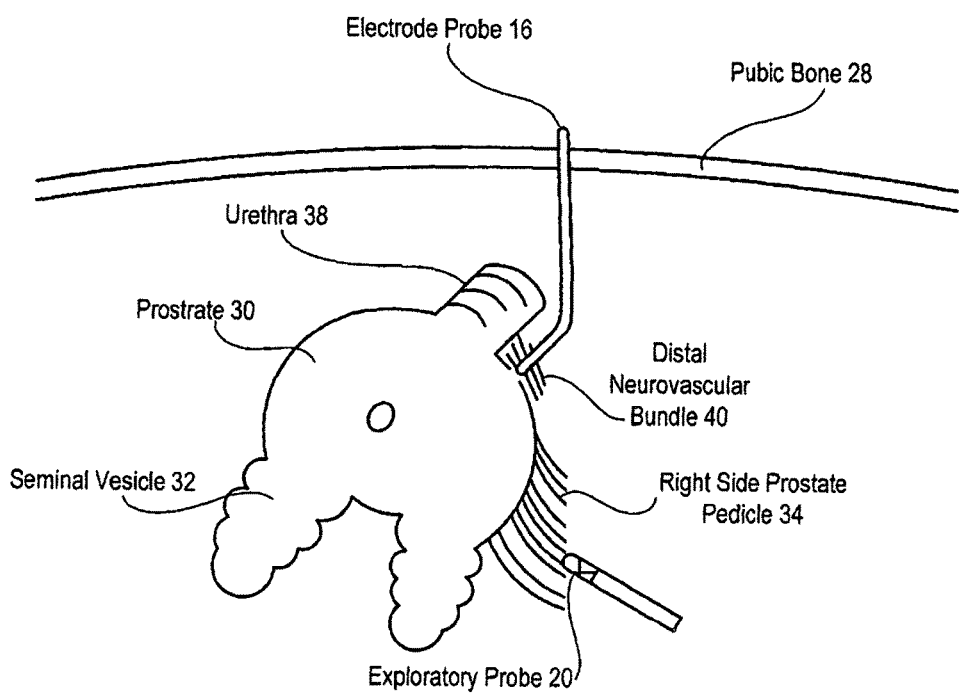
FIG. 4 depicts an exploratory probe providing an electrical current along a presumed pathway of the nerve to map the nerve pathway.

Referring now to FIG. 4, an exploratory probe 20 providing an electrical current along a presumed pathway of the nerve to map the nerve pathway is depicted. Electrode probe 16 attaches at the apex of prostate 30 near where the urethra enters the penis. The position at the apex of prostate 30 is a consistent position for the distal NVB just before it enters into the penis. Electrode probe 16 is of appropriate length to attach at the apex of prostate 30 and is pre-fabricated into handle 10 and catheter 14 to make connection of the recording probe to the body simple and reliable. Once probe 16 is connected to the body at the consistent location of the NVB, electrical stimulation is achieved by delivering a low stimulation current through an exploratory probe 20, such as a laparoscopic or robotic bipolar instrument. The NVB (e.g. erectile nerves) is stimulated more or less depending on the proximity of the exploratory probe. Initial searching for the nerve is performed at relatively high stimulus intensities, such as about 3.5 milliamp, or even possibly as high as 10 milliamp of current. Searching is performed by placing exploratory probe 20 at several places around the presumed pathway of the nerve and listening for an auditory response from the speaker as well as a visual confirmation on user interface 24 as provided by analyzer 18 that reflects the strength of the electrical signal received at probe 16. Once the nerve's general pathway is mapped, the stimulus intensity provided at exploratory probe 20 is reduced, such as to a level of one-half a milliamp, to map the nerve's location more precisely.

Figure 5:
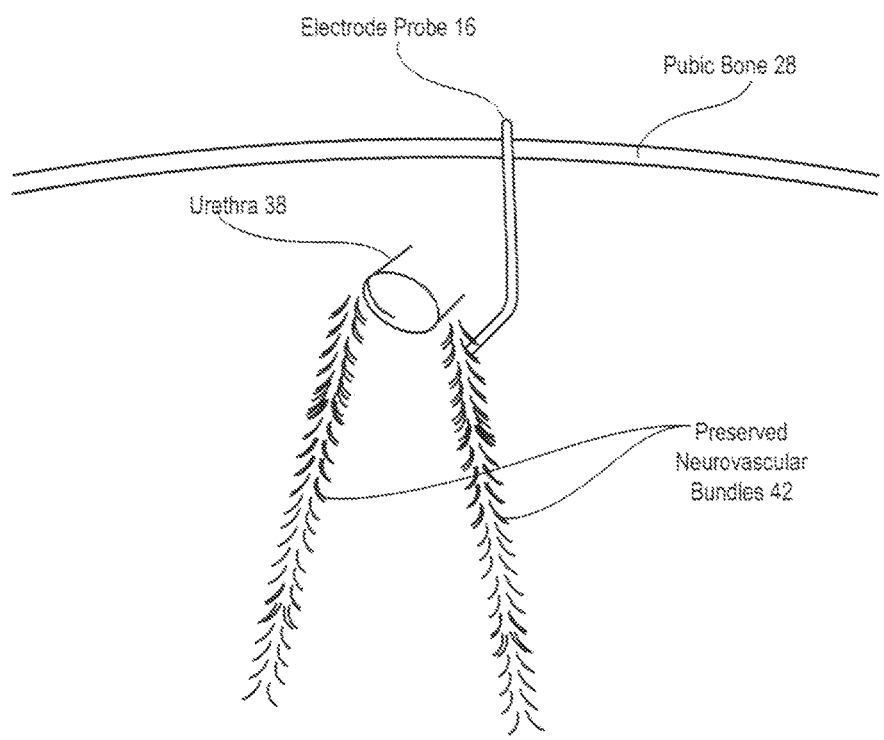
FIG. 5 depicts a postoperative position of the nerve pathway after removal of a prostate gland.

Referring now to FIG. 5, a postoperative position of the nerve pathway after removal of a prostate gland is depicted. Throughout dissection of the prostate, exploratory probe 20 is used, by selectively repositioning it and repeatedly introducing an electrical signal at a predetermined strength, to re-map and confirm the position of NVB 40. The objective is to confirm the location of the erectile nerves so that tissue may be selectively preserved or removed depending on the aggressiveness of the cancer. Although the example presents preservation of the nerves to the NVB during a prostatectomy, other types of nerves may be identified and preserved within the abdominal cavity or other body cavities, depending upon the surgical procedure being performed.

As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A method of mapping a location of a nerve within a body cavity of a body, the method comprising:
   a) providing at least one flexible electrode probe configured to be inserted into the body cavity through a surface of the body, the at least one flexible electrode probe being: (a)(i) positionable by grasping and pulling the at least one flexible electrode probe with an independent laparoscopic device and (a)(ii) configured to couple to body tissue under the influence of the independent laparoscopic device, the body tissue being included within the body cavity;
   b) disposing the independent laparoscopic device into the body cavity;
   c) inserting the at least one flexible electrode probe into the body cavity to a position accessible by the independent laparoscopic device and manipulating the independent laparoscopic device to temporarily attach the at least one flexible electrode probe to the body tissue;
   d) inserting an exploratory probe, which is separate and distinct from the at least one flexible electrode probe, into the body cavity;
   e) periodically introducing a first electrical signal via the exploratory probe to the body tissue as the exploratory probe is moved (e)(i) to multiple locations within the body cavity that are proximal to the at least one flexible electrode probe, and (e)(ii) while simultaneously the at least one flexible electrode probe is temporarily attached to the body tissue;

f) in response to periodically introducing the first electric signal as the exploratory probe is moved to multiple locations within the body cavity, sensing a second electrical signal via the at least one flexible electrode probe;

g) providing an analyzer which is (g)(i) interfaced with the at least one flexible electrode probe, and (g)(ii) configured to provide data that corresponds to proximity of the exploratory probe to the nerve;

h) providing the data, via the analyzer, in response to sensing the second electrical signal via the at least one flexible electrode probe; and i) in response to providing the data, determining, via the analyzer, the location of the nerve.

2. The method of claim 1, wherein the at least one flexible electrode probe includes a first flexible electrode probe and a second flexible electrode probe, the first flexible electrode probe being configured to be couplable near a first nerve and the second flexible electrode probe being configured to be couplable near a second nerve to permit mapping of the second selected nerve immediately subsequent to mapping of the first nerve without removal and repositioning of the first flexible electrode probe.

3. The method of claim 1, wherein:
manipulating the independent, grasping, surgical laparoscopic device (36) to temporarily attach the at least one flexible wire electrode probe (16) to tissue within the body cavity comprises manipulating the independent, grasping, surgical laparoscopic device (36) to temporarily attach the at least one flexible wire electrode probe (16) to an apex of a prostate gland;
the internal nerve is an erectile nerve adjacent the prostate gland.

4. A method of mapping a location of a nerve within a body cavity of a body, the method comprising:

a) providing a flexible electrode probe configured to be inserted into the body cavity through a surface of the body, the flexible electrode probe being: (a)(i) positionable by grasping and pulling the flexible electrode probe with an independent laparoscopic device and (a)(ii) configured to temporarily attach to body tissue under the influence of the independent laparoscopic device, the body tissue being included within the body cavity;

b) providing the independent laparoscopic device;

c) providing an exploratory probe, which is separate and distinct from the flexible electrode probe, wherein:
the exploratory probe is configured to be disposed in the body cavity and periodically introduce a first electrical signal via the exploratory probe to the body tissue as the exploratory probe is moved (i) to multiple locations within the body cavity that are proximal to the flexible electrode probe, and (ii) while simultaneously the flexible electrode probe is temporarily attached to the body tissue;
in response to periodically introducing the first electric signal as the exploratory probe is moved to multiple locations within the body cavity, the flexible electrode probe is configured to sense a second electrical signal;

d) providing an analyzer configured to:
interface with the flexible electrode probe;
provide data that corresponds to proximity of the exploratory probe to the nerve in response to sensing the second electrical signal via the flexible electrode probe;
in response to providing the data, determine the location of the nerve.

* * * * *

UNITED STATES PATENT AND TRADEMARK OFFICE
CERTIFICATE OF CORRECTION

PATENT NO. : 10,045,704 B2
APPLICATION NO. : 13/290035
DATED : August 14, 2018
INVENTOR(S) : Randy Fagin et al.

Page 1 of 1

It is certified that error appears in the above-identified patent and that said Letters Patent is hereby corrected as shown below:

In the Claims

Column 7 Claim 2, Line 24, "second selected nerve immediately subsequent to mapping" should be --second nerve immediately subsequent to mapping--.

Signed and Sealed this
Sixth Day of November, 2018

Andrei Iancu
*Director of the United States Patent and Trademark Office*